United States Patent [19]
Hamilton

[11] Patent Number: 5,787,882
[45] Date of Patent: Aug. 4, 1998

[54] DEMAND VALVE RESUSCITATOR

[75] Inventor: Robert M. Hamilton, Alta Mesa, Calif.

[73] Assignee: Computer Assisted Engineering, Orange, Calif.

[21] Appl. No.: 667,411

[22] Filed: Jun. 21, 1996

[51] Int. Cl.$^6$ ............ A62B 9/04; A62B 7/04; A61M 16/00; F16K 31/26

[52] U.S. Cl. .................. 128/204.26; 128/205.24

[58] Field of Search ............. 128/204.26, 205.24, 128/205.25, 207.12

[56] References Cited

U.S. PATENT DOCUMENTS

| | | | |
|---|---|---|---|
| 2,418,034 | 3/1947 | Kizaur | 128/204.26 |
| 3,362,404 | 1/1968 | Beasley | 128/204.26 |
| 3,717,147 | 2/1973 | Flynn | 128/204.25 |
| 3,795,257 | 3/1974 | Fabish et al. | 137/491 |
| 3,874,378 | 4/1975 | Isaacson et al. | 128/205.23 |
| 3,995,625 | 12/1976 | Needham | 128/204.26 |
| 4,374,521 | 2/1983 | Nelson et al. | 128/204.26 |
| 4,898,174 | 2/1990 | Fangrow, Jr. | 128/204.26 |
| 5,425,358 | 6/1995 | McGrail et al. | 128/205.24 |
| 5,537,999 | 7/1996 | Dearman et al. | 128/205.14 |

*Primary Examiner*—Kimberly L. Asher
*Attorney, Agent, or Firm*—Harold L. Jackson

[57] ABSTRACT

A demand valve resuscitator includes an inlet for connection to a pressurized source of breathable gas, such as oxygen, and an outlet for connection to a patient's airway. A normally-closed-pressure-actuated main valve is positioned between the inlet port and an inhalation chamber for controlling the demand mode of operation. A main valve controller operates the main valve in response to a reduced pressure in the inhalation chamber resulting from the commencement of spontaneous breathing by the patient. The manual operating mode, i.e., not dependent upon the patient breathing spontaneously, is controlled by a bypass valve which supplies gas to the patient independently of the main valve. A manually adjustable pressure relief valve sets the peak gas pressure. Another manual control permits the operator to preset the maximum opening of the bypass valve and therefore the flow rate of gas to the patient.

25 Claims, 6 Drawing Sheets

DEMAND VALVE RESUSCITATOR

BACKGROUND OF THE INVENTION

1. Field of the Invention

The present invention relates to a resuscitation demand valve and more particularly to such a valve which will supply oxygen or an air/oxygen mixture to the airway of a patient or other individual as determined by an operator or as demanded when the patient commences breathing on his own.

2. Description of the Prior Art

In instances of cardiac arrest or cessation of spontaneous breathing, emergency life support measures require a means to revive a patient's breathing function. This is most often accomplished by the use of a manually operated resuscitation device. These devices administer oxygen in response to the manual operation of the device. When spontaneous breathing is restored, it is desirable to continue administration of oxygen on a demand basis.

The early devices for administering oxygen to such patients or individuals are typified by that described in U.S. Pat. No. 3,795,257. The early requirements were to provide a flow capacity of 160 LPM (liters per minute) and a maximum pressure of 40 cm $H_2O$ (centimeters of water). The patented units utilized an manually-operated control mechanism to load the sensing diaphragm so as to provide the prescribed pressure control at the outlet. The units were fitted with a combination inhalation/exhalation valve that was easily removed for cleaning.

These units were standard equipment for emergency medical teams through out the United Stated and other countries. While the high flow rates at the prescribed pressure were quite effective at achieving good ventilation, such flow rates often caused problems with gas (oxygen) being forced into the patient's stomach and not all medical experts agreed on the pressure and flow rate limits.

With the experience of twenty years the requirements were modified to require flow rates in the manual mode of no more than 40 LPM. It was also deemed desirable to have a relief device to protect against excess pressure.

Figure 1:
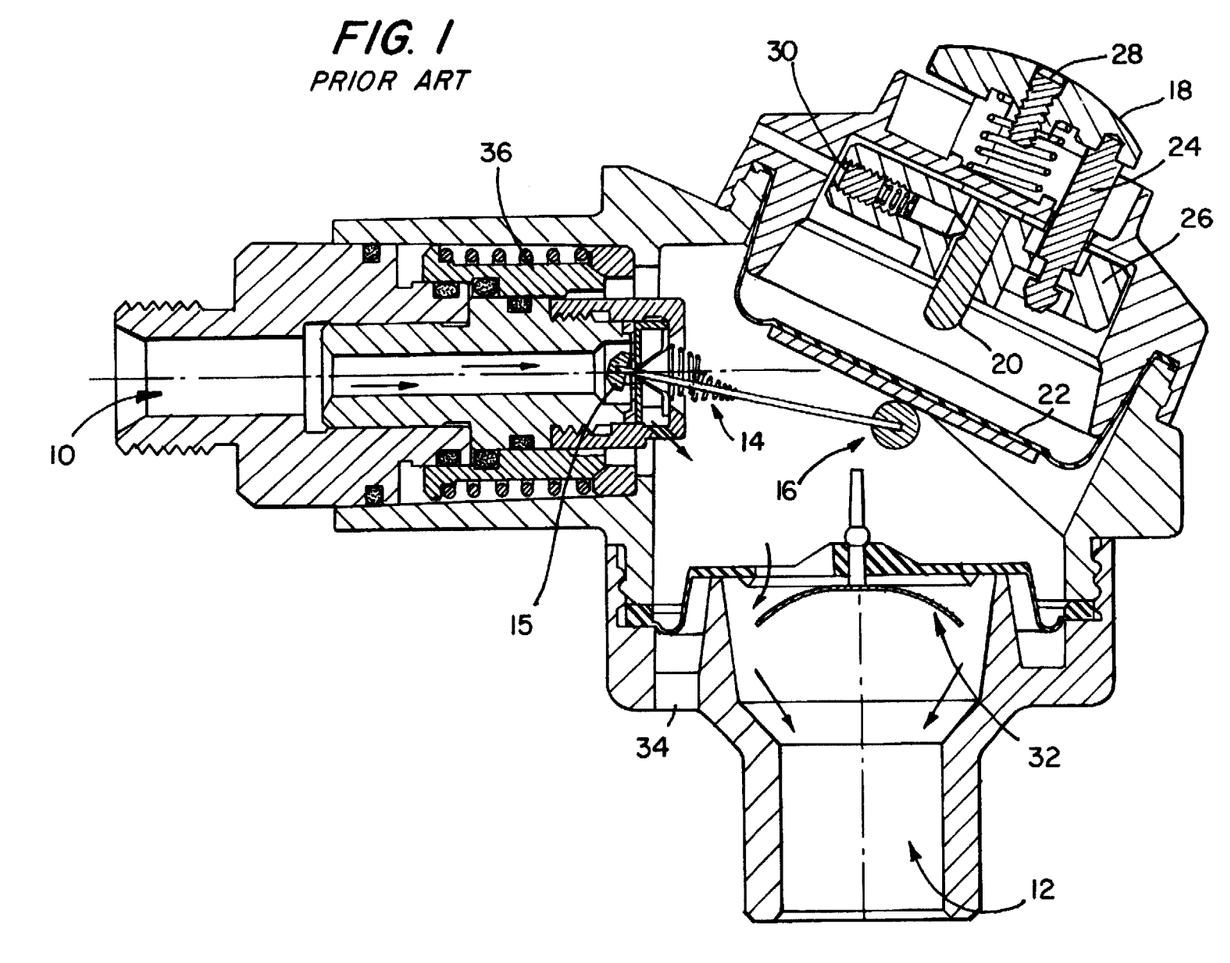
FIG. 1 is a cross-sectional view of a prior art valve.

The first of the new generation of valves is illustrated by the "tilt valve" unit shown in FIG. 1. The problem faced by designers was to limit flow rate to 40 LPM maximum, in the manual mode, while providing a minimum of 100 LPM in the demand mode. This was accomplished by the use of a direct acting valve that had a limited opening during the manual mode but was allowed to open fully in the demand mode. This unit also had a relief valve to limit maximum pressure and an anti-suffocation valve to prevent patient suffocation in the event that the patient was left unattended, the oxygen depleted, and the mask left fixed to the patient's face.

The prior art demand "tilt valve" of FIG. 1 includes an inlet 10 adapted to be connected to a pressurized source of oxygen or a mixture of oxygen and air and an outlet 12 adapted to be placed within the patient's mouth or otherwise connected to his or her airway. A normally-closed-main valve 14 including a moveable valve member 15, is disposed between the inlet and outlet. The main valve responds to the position of a spring biased actuating arm 16. The actuating arm is moved by a button 18, to supply the oxygen to the patient's airway, in the manual mode. Depression of the button 18 moves the cylindrical post 20 downwardly against the plate reinforced diaphragm 22, via elongated pin 24 and disc 26. Downward movement of the diaphragm 22 pivots the actuating arm 16 and opens the main valve 14. A set screw 28 (set at the factory) sets the limit of travel of the operating button 18 and thus the degree of opening for the main valve 14, which in turn sets the maximum flow rate of oxygen during the manual mode.

A spring biased set screw 30, also set at the factory, determines the maximum allowable pressure during the manual mode. The distal end of the set screw seats in a notch in the post 20 as illustrated. When the pressure on the diaphragm 22 exceeds the allowable maximum (during the manual mode) the post 20 forces the terminal end of the set screw out of the notch and allows the post (and the diaphragm) to move upwardly, closing the main valve.

In the demand mode, a sub-atmospheric pressure below the diaphragm 22 (as a result of the patient commencing to breath spontaneously) causes the diaphragm 22 to move downwardly and forces the actuating arm to open the main valve. The space above the diaphragm is vented to atmosphere. A combination inhalation/ exhalation valve 32 allows exhaled air to be exhausted through ports 34.

An anti-suffocation valve 36 is opened when the oxygen in the pressurized source is deplete.

The above prior art devices possess several shortcomings. First, the units are not designed to allow the operator to adjust the flow rate in the manual mode. However, it is desirable to reduce the peak flow rate when administering oxygen to small children to accommodate their smaller lung volumes. It may also be desirable to reduce the flow rate when administering oxygen to adults with an airway obstruction to minimize the pressure build up across the obstruction. Thus, there is a need for a device which will allow the operator to adjust the flow rate when administering oxygen in the manual mode.

Second, the prior art devices do not allow the operator to adjust the peak pressure in the manual mode. Control of the peak pressure by the operator may be necessary to prevent excess air from being forced into a patient's stomach.

Third, the above devices do not have an audible alarm to inform the operator that the peak pressure limit has been exceeded as a result of a restricted airway or the completion of the inflation cycle.

There is need for a demand valve resuscitator which provides the above features.

SUMMARY OF THE INVENTION

A demand valve resuscitator in accordance with the present invention includes housing having an inlet port adapted to be connected to a pressurized source of oxygen or mixture of oxygen and air ("breathable gas"), an outlet port adapted to be connected to a patient's or individual's airway, i.e., an inhalation chamber positioned between the inlet and outlet ports and an exhalation port.

The demand mode of operation is controlled by a normally-closed-pressure-actuated main valve which is positioned between the inlet port and the inhalation chamber. A main valve controller selectively opens the main valve in response to a reduced pressure in the inhalation chamber, i.e. as a result of the commencement of spontaneous breathing by the individual.

The manual mode of operation is controlled by a manually-operated bypass valve connected between the inlet and the inhalation chamber for supplying gas from the source to the patient independently of the main valve. A pressure regulator, in fluid communication with the inhalation chamber, sets the peak gas pressure and is preferably manually controllable so that an operator can adjust the pressure setting within limits set at the factory. A manual control for permitting the operator to preset the maximum opening of the bypass valve and therefore the maximum gas flow rate is also preferably included. An inhalation/ exhalation check valve is disposed between the inhalation chamber, the outlet and exhalation ports for channeling gas from the inhalation chamber into the individual's airway and for venting exhaled gas through the outlet port. An audible alarm is preferably inserted in the gas flow path from the inhalation chamber to the pressure regulator to inform the operator that the allowable peak pressure has been exceeded.

The construction and operation of the present invention may best be understood by reference to the following description in conjunction with the attached drawings wherein like components are designated with the same reference numerals in the several figures.

DESCRIPTION OF THE PREFERRED EMBODIMENT

Figures 2, 11:
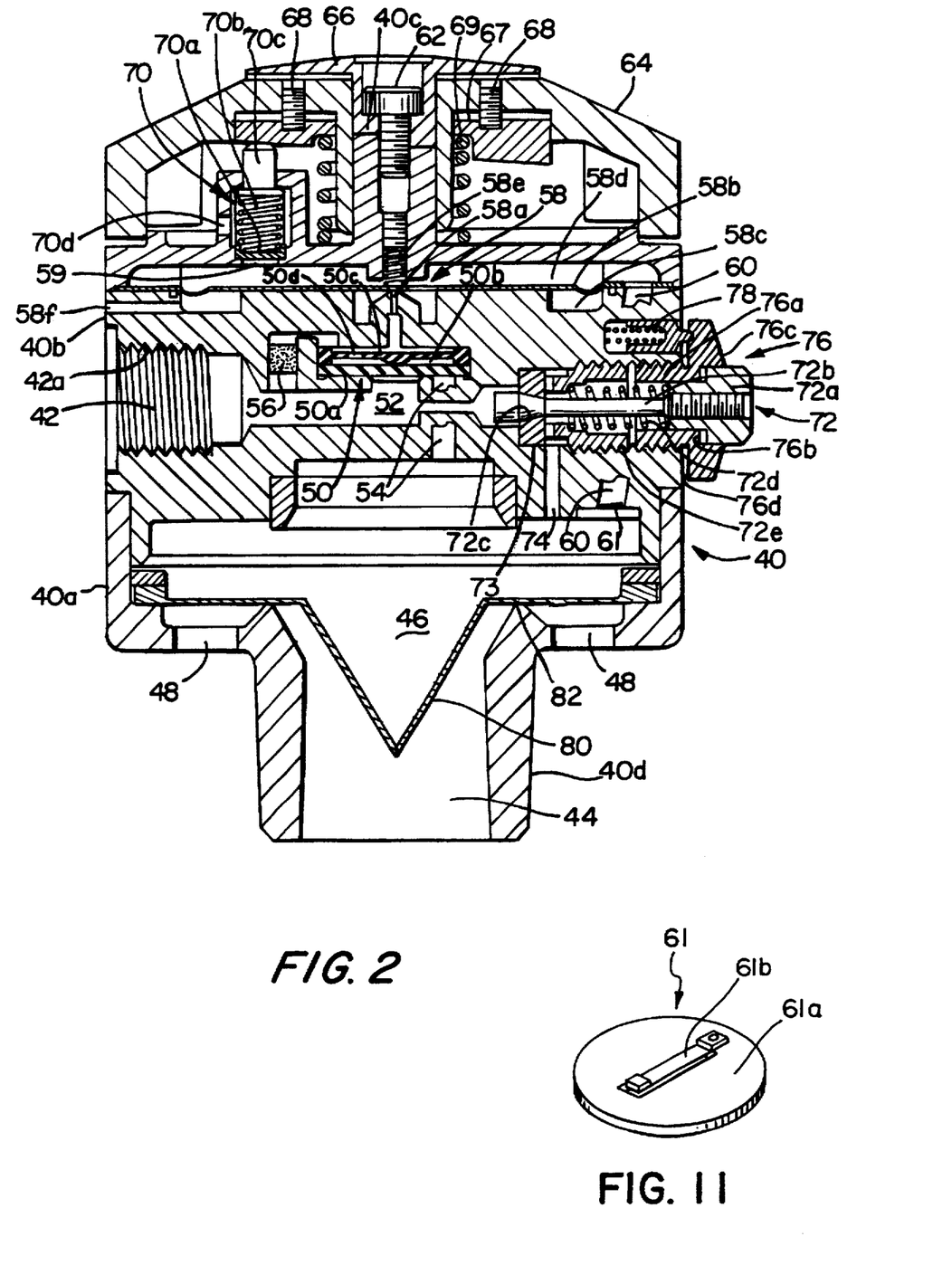
FIG. 2 is a cross-sectional view of a demand valve resuscitator in accordance with the present invention.
FIG. 11 is a perspective view of an audible alarm which may be placed in series with the maximum pressure relief valve.

Referring now to FIG. 2, the demand valve, in accordance with this invention, includes housing 40 having an inlet port 42, an inhalation chamber 46, an outlet port 44, and exhalation ports 48. The inlet port is adapted to be connected to a source of breathable gas, such as pure oxygen or a mixture of air and oxygen, under pressure via threads 42a. The housing is formed in two sections with the lower section 40a threaded to the upper section 42b. The lower section includes a depending tubular section 40d surrounding the outlet port 44 which is adapted to be connected to a face mask or endotracheal tube interfaced with the patient's airway. The outer surface of the depending tubular section 40d is arranged to fit within a corresponding opening in a conventional face mask fitted over the patient's face while the inner diameter of this section is arranged to receive the proximal end of a contentional endotracheal tube disposed within the patient's trachea. The lower section may be made of plastic and provides an inexpensive outlet which may be disposed of (and replaced) after use with a patient.

A normally-closed main valve 50, operable in the demand mode, is positioned in series with the inlet port and the outlet port, via passageways 52 and 54. The main valve is in the form of a diaphragm valve (e.g., first diaphragm valve) with a flexible diaphragm 50a extending over seats formed at the ends of passageways 52 and 54, as illustrated. The portion of passageway 52, adjacent the diaphragm 50a, forms a first chamber. A second chamber 50b extends on the other side of the diaphragm 50. The area of the diaphragm exposed to the second chamber is greater than the diaphragm area exposed to the first chamber. A restrictor 56 bleeds gas from the pressurized source (inlet 42) into the second chamber 50b to thereby maintain the pressure actuated valve 50 in a normally closed position since, at equilibrium, with a zero pressure differential across the diaphragm, the diaphragm is forced against the seats formed at the ends of passageways 52 and 54. A rigid disk 50c supports the center and peripheral edge of the diaphragm 50a. An opening 50d in the disk 50c provides fluid communication between the passageway 52 and the chamber 50b, via the restrictor 56.

A second diaphragm or pilot valve 58 controls the operation of the main valve 50 by opening and closing a pilot port 58a via a sensing diaphragm 58b. The valve 58 includes first and second chambers (58c, 58d) disposed below and above the sensing diaphragm, respectively, as shown. The first chamber 58c is vented to atmosphere, via vent port 58f. The second chamber 58d is in fluid communication with the inhalation chamber 46, via passageway 60. An audible alarm 61 in the form of a slotted metallic disc 61a with a metallic reed 61b secured at one end of the disc and extending over the slot, is positioned in a counterbore at the end of passageway 60 adjacent the inhalation chamber. The alarm is shown in more detail in FIG. 11 and the operation of the alarm will be explained in more detail in connection with the description of a pressure relief valve 70.

The sensing diaphragm 58b is biased to close the pilot port 58a by means of a spring 58e. The spring 58e is retained in a hollowed end section of a bolt 62 received in a threaded opening in the upper section 40b of the housing 40, as illustrated.

The bolt 62 also secures a manually operable maximum pressure adjusting knob 64 and a detent positioning cap 66. The knob 64 is rotatably mounted on an upstanding cylindrical post 40c of the upper section 40b of the housing. The cap is keyed to the post 40c and thus does not rotate with the knob 64. An annular cam 67 is carried by the knob 64, via set screws 68 and spring 69. The set screws 68 are threaded into holes in the knob 65, with the distal ends thereof projecting into blind holes in the upper surface of the cam 67, as shown.

A pressure relief valve 70, for controlling the maximum allowable inhalation chamber or outlet pressure, includes a valve plate 70a. The plate 70a is biased, via spring 70b, against a seat surrounding an opening 59 which is in fluid communication with the second chamber 58d of the second diaphragm valve 58. The lower surface of the cam 67 engages a pressure setting rod 70c of the relief valve. A vent port 70d vents gas from the chamber 58d and the inhalation chamber to atmosphere when the relief valve is open.

The maximum or peak inhalation chamber pressure is determined by the compressive force of the spring 70b on the valve plate 70a and this force is set by the angular position of the cam 67 within a range as determined by the set screws 68. The set screws 68 will normally be adjusted at the factory to allow the operator to adjust the peak pressure within an allowable range, say from 20 to 40 cm $H_2O$. When the peak pressure, as set by the cam 67 is exceeded, gas flow through the passageway 60, creates an audible alarm via the vibrating reed 61b of the alarm 61. The reed 61b can be tuned, by appropriate adjustment of its dimension and elasticity, to resonate at a desired frequency, i.e., 1000–2000 Hz.

Figures 3, 4:
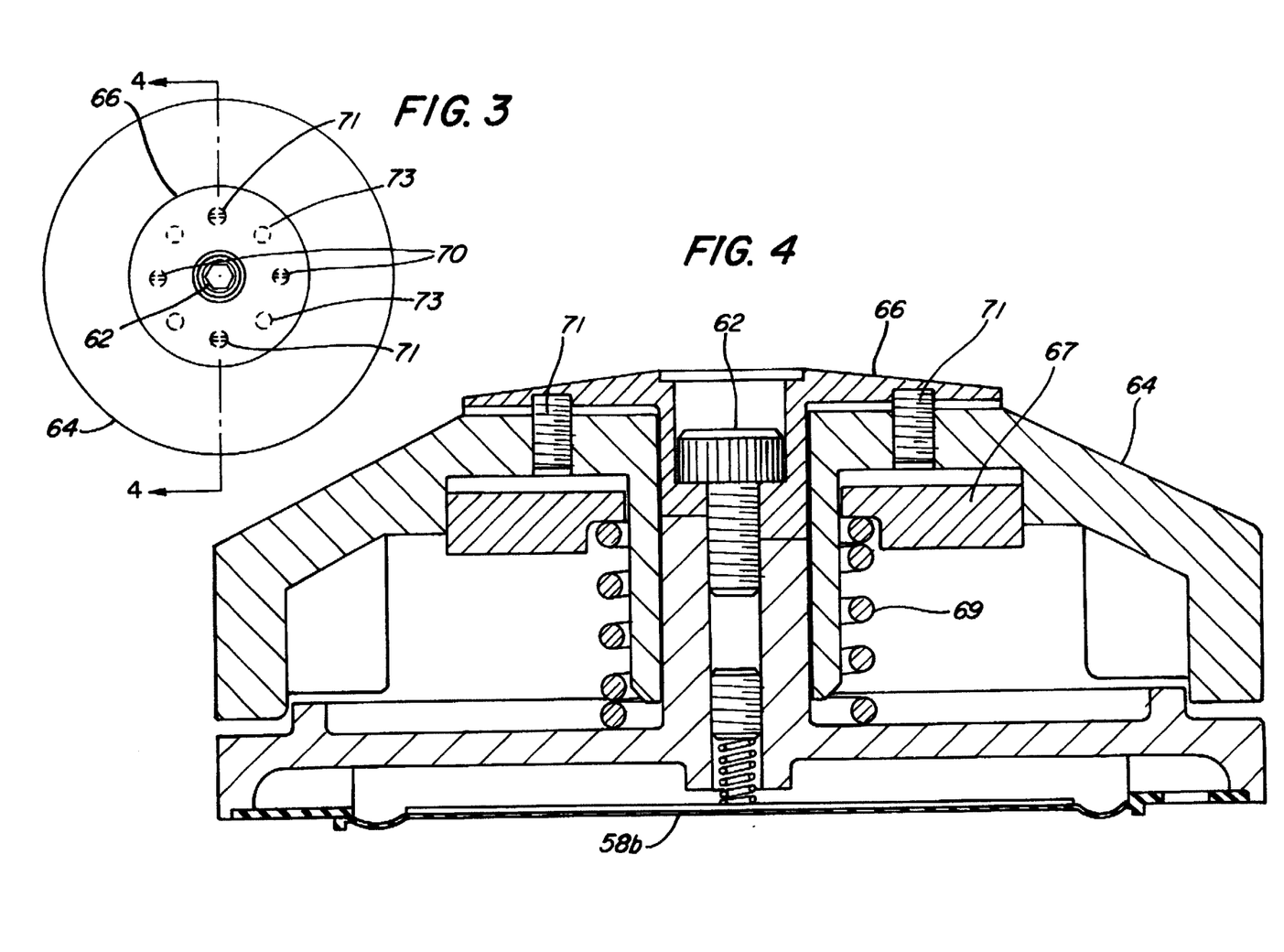
FIG. 3 is a top plan view of the valve of FIG. 2.
FIG. 4 is an enlarged cross-sectional view of the upper portion of the valve of FIG. 2 taken along lines 4—4 of FIG. 3.

A second set of set screws 71, shown in FIGS. 3 and 4, are threaded into bores in the top of the knob 64 and arranged to seat in two of four sets of blind holes 73 extending upwardly from the lower surface of the cap 66. An operator may turn the knob 64 in forty-five degree increments to reposition the cam 67 relative to the relief valve by first depressing the knob to disengage the set screws 71 from the cap 66.

A bypass valve, indicated generally at 72, for use in the manual mode, includes an actuating button 72a threaded on the proximal end of an elongated valve member 72b, as shown. The distal end of the valve member 72b has a tapered portion which engages a conical seat 72c formed in a bushing 73 situated at the distal end of the inlet passageway 52. A spring 72d extends between another bushing 72e, threaded into a bore within the lower section 40a of the housing, and a shoulder on the actuating button 72a, as shown. The bypass valve is normally in a closed position as a result of the spring 72d. Manual depression of the actuating button 72 (toward the inlet port) opens the valve, channeling the breathable gas from the inlet 42 to the inhalation chamber 46, and the outlet port 44, via passageways 52 and 74.

The flow rate of gas through the bypass valve 72 is determined by the extent of the axial movement of the valve member 72b (toward the inlet). An adjustable stop member 76, for controlling the extent of the axial movement of the bypass valve member 72b, includes a tubular section 76a threaded into the housing. The tubular section 76a surrounds an inner end of the button 72a. The stop member further includes an annular shoulder 76b, facing a cooperating shoulder on the button 72a, and a knob 76c. The inner face 76d of the knob 76c includes three (or more) depressions 76e, spaced at 90°, for example, which cooperate with a spring biased detent 78, to allow the knob to be rotated 180° (or more) in three (or more) discrete steps. The adjustable stop member 76 and the valve member 72b may be arranged to allow the operator to selectively set the flow rate (in the demand mode) at 15, 25, and 40 LPM, for example.

Figure 10:
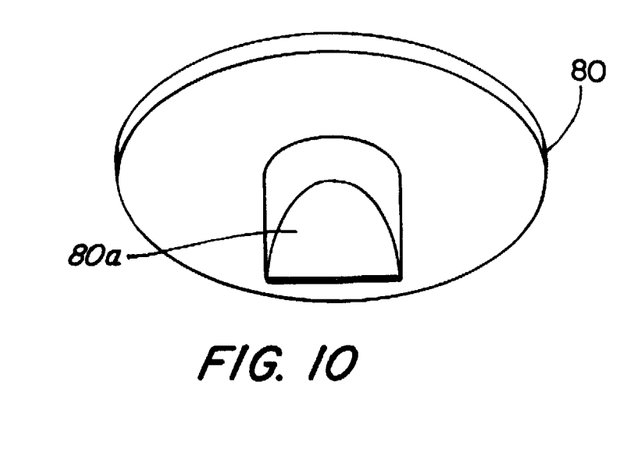
FIG. 10 is a perspective view of the inhalation and exhalation valve.

An outlet or inhalation/exhalation valve 80 in the form of a common flexible-diaphragm duck valve, as shown in FIG. 10, extends between the inhalation chamber 46 and the outlet and exhalation ports. As will be explained more fully with respect to FIGS. 5-8, the flexible diaphragm 80 is normally seated against an annular seat 82 on the lower housing section 40a to close the exhalation ports 48. A center section 80a (FIG. 10) of the diaphragm is also normally closed, but opens during the inhalation cycle to pass gas from the pressurized source to the patient's or individual's airway. The center section 80a closes and the diaphragm moves above the seat 82 during the exhalation cycle to vent exhaled air (back pressure) to the atmosphere through exhalation ports 48.

Figure 5:
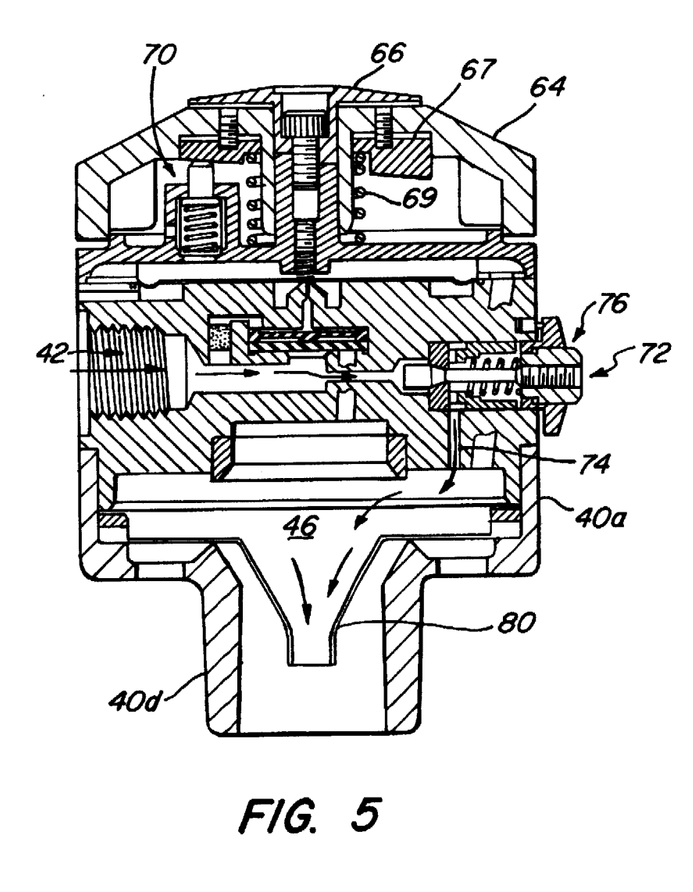
FIGS. 5, 6 and 7 are cross-sectional views showing the valve operating in the manual mode during the inflation, deflation and alarm cycles, respectively.
Figure 6:
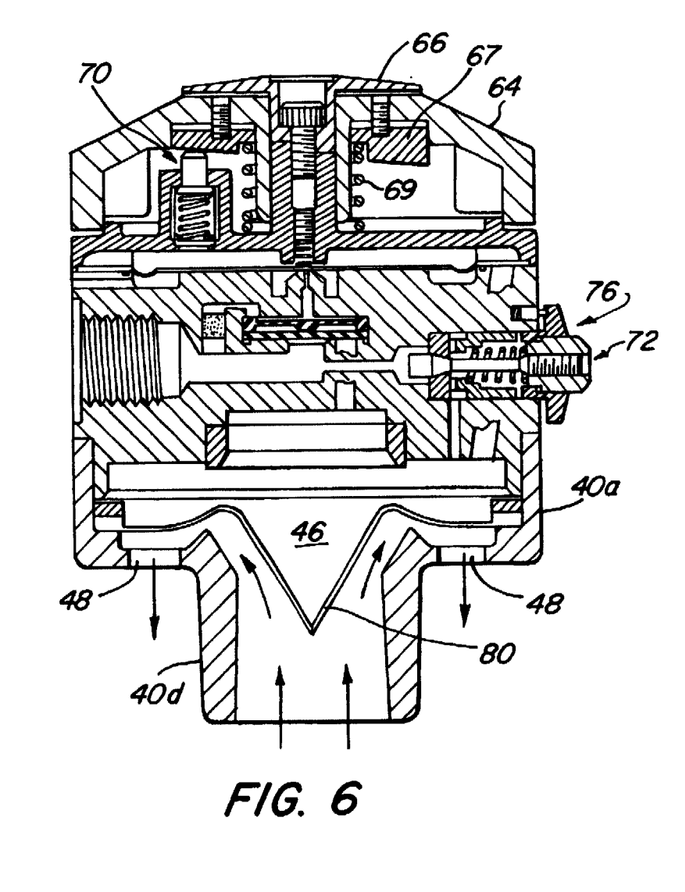

Prior to operating the resuscitator a source of pressurized oxygen or other breathable gas is connected to the inlet port 42. Assuming that the patient or individual to receive the oxygen is not breathing, the operator may set the flow rate of oxygen by turning the flow rate knob 76 to the appropriate position. The peak pressure may also need to be set, via the knob 64. The outlet end 40d of the housing is then connected to a face mask or an endotracheal tube, which interfaces with the patient's airway, and the actuating button 72a depressed oxygen will then flow from the pressurized source into the individual's airway as illustrated by the arrows of FIG. 5. The actuating button 72a is released at the end of the inflation cycle allowing air within the individual's lungs to be expelled through the outlet ports 48, as is illustrated in FIG. 6. This mode is conventionally referred to as the manual mode.

Figure 7:
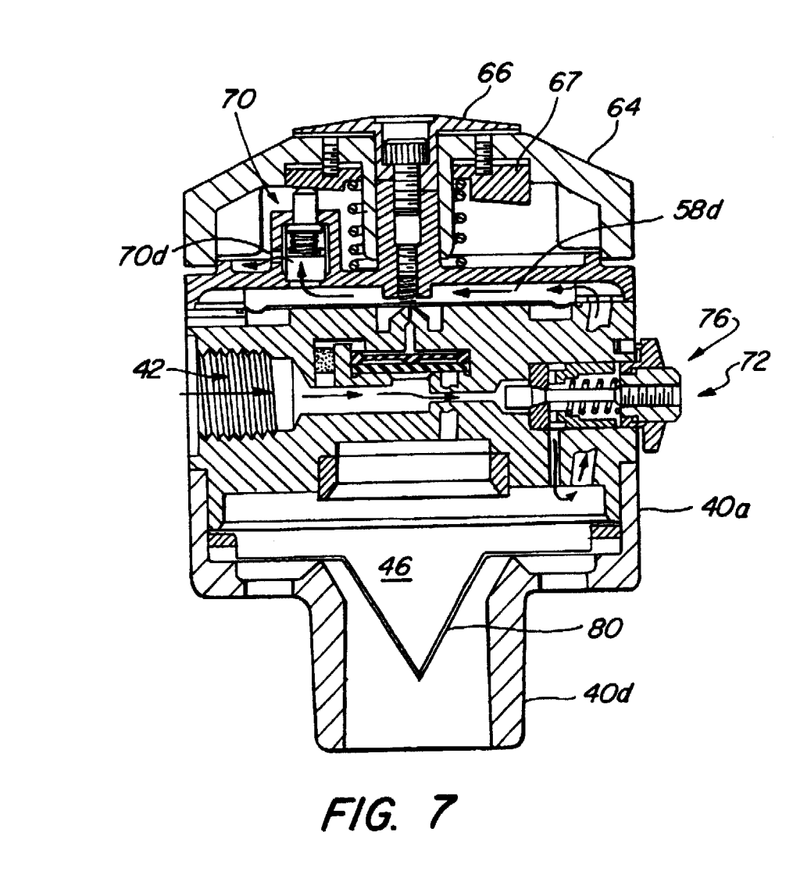

FIG. 7 illustrates, via arrows, the gas flow pattern when the peak pressure has been exceeded.

Figure 8:
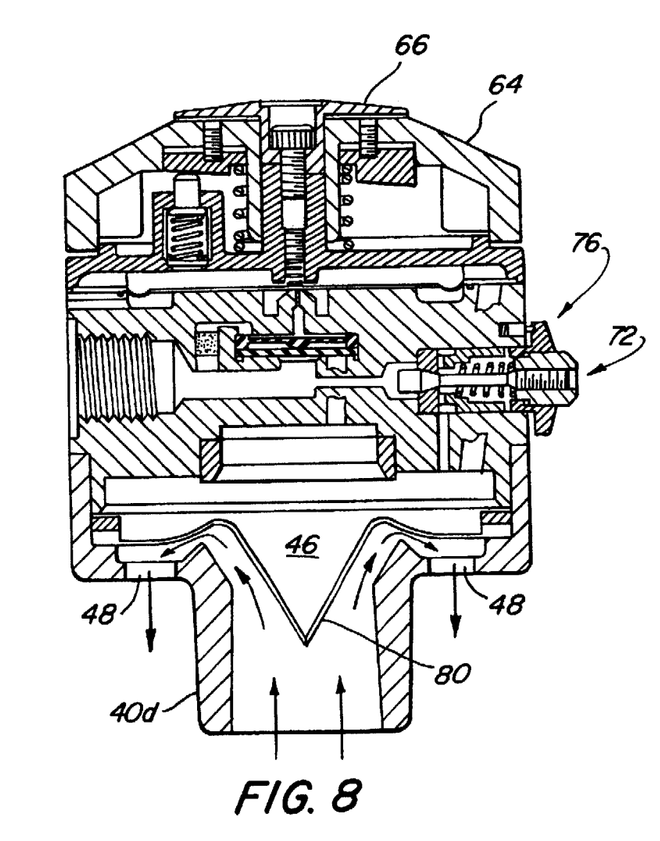
FIGS. 8 and 9 are cross-sectional views of the valve in the demand mode during the exhalation and inhalation half cycles, respectively.
Figure 9:
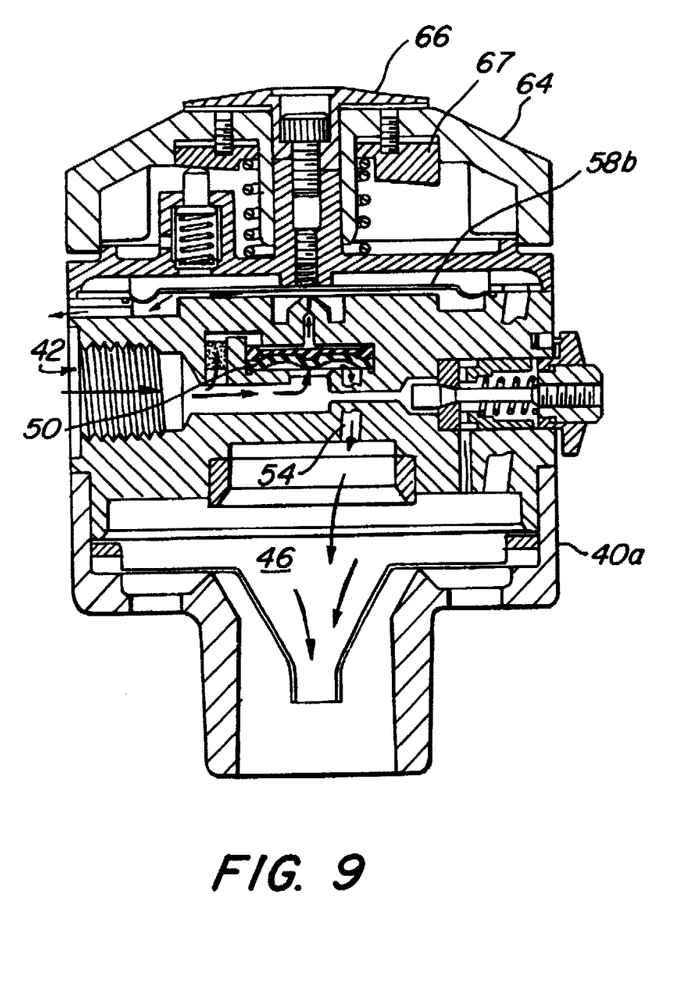

When the individual commences breathing on his own and starts to inhale, e.g., the demand mode, the pressure in the inhalation chamber falls below atmospheric pressure. This causes the sensing diaphragm 58b to move away from the pilot valve port 58a allowing the pressure on the opposite side of main valve diaphragm 50a e.g., in chamber 50b, to decay due to the limited flow rate through the restrictor 56. When the differential pressure across the diaphragm 50a reaches a preset value, the main valve 50 opens and permits flow from the inlet port to the inhalation chamber and the outlet port, as is illustrated by the arrows in FIG. 9. When the pressure at the outlet port or inhalation chamber 46 rises to atmospheric, the sensing diaphragm moves to close the pilot valve port 58a. This action results in the re-establishment of the inlet pressure on the opposite side of the main valve diaphragm 50a e.g., in chamber 50b, blocking flow between the inlet port and the inhalation chamber and the outlet FIG. 8 illustrates the exhalation flow.

There has thus been described a novel demand valve resuscitator which performs the required manual and demand functions and in addition provides (1) an adjustable flow rate control in the manual mode, (2) an adjustable pressure limit in both the manual and demand modes, and an audible alarm when the peak pressure limit has been exceeded.

Various modifications and additions to the disclosed valve will occur to those skilled in the art without involving any departure from the spirit and scope of the invention as called for in the appended claims.

What is claimed is:

1. A demand valve resuscitator for controlling the flow of breathable gas from a pressurized source to an individual comprising:

a) a housing having an inlet port adapted to be connected to the pressurized gas source, an outlet port adapted to be connected to the individual's airway, an inhalation chamber disposed between the inlet and outlet ports and an exhalation port;

b) a normally-closed-pressure-actuated main valve disposed in the housing between the inlet port and the inhalation chamber;

c) a main valve controller disposed in the housing and responsive to the pressure in the inhalation chamber for selectively opening and closing the main valve;

d) a pressure relief valve disposed in the housing and in fluid communication with the inhalation chamber for setting the maximum allowable gas pressure within the inhalation chamber, the pressure relief valve including a manual control for adjusting the pressure setting of the pressure relief valve;

e) a manually-operated bypass valve disposed in the housing for connecting the inlet to the inhalation chamber to supply gas from the pressurized source to the inhalation chamber independently of the main valve, the bypass valve including a manual control for presetting the maximum opening of the bypass valve to control the maximum flow rate of gas from the pressurized source to the inhalation chamber; and f) an inhalation/exhalation check valve disposed between the inhalation chamber and the outlet and exhalation ports for allowing gas from the pressurized source to pass from the inhalation chamber through the outlet and enter the individual's lungs and for venting the individual's exhaled gas to the outlet port.

2. The invention of claim 1 further including an alarm responsive to the pressure relief valve for providing an audible alarm when the pressure in the inhalation chamber exceeds the preset maximum allowable pressure.

3. The invention of claim 2 wherein both chambers of the first diaphragm valve are connected to the inlet port, the connection to the second chamber including a restrictor for restricting the flow rate.

4. The invention of claim 3 wherein the main valve controller includes a normally closed second valve which opens the second chamber of the first diaphragm valve to atmosphere when the pressure within the inhalation chamber is below a predetermined value to allow the main valve to open and supply demand gas to the individual.

5. The invention of claim 4 wherein the second valve is a diaphragm valve with first and second chambers on opposite sides of the diaphragm, the first chamber of the second valve being vented to atmosphere and the second chamber thereof being in fluid communication with the inhalation chamber, whereby the second valve is in the open position when the pressure within the inhalation chamber is sub-atmospheric.

6. The invention of claim 5 wherein the manual control for the pressure relief valve includes a manually moveable cam which sets the maximum allowable pressure in accordance with the position of the cam relative to the relief valve.

7. The invention of claim 6 wherein the relief valve is spring biased and the cam adjusts the force of the spring and thereby the pressure required to open the relief valve.

8. The invention of claim 7 wherein the cam is annular in shape with the opening force varying with the angular position of the cam, the manual control further including a rotatable knob connected to the cam for adjusting the angular position thereof.

9. The invention of claim 2 wherein the alarm is in the form of a slotted disc with a reed affixed at one end to the disc and extending over the slot.

10. The invention of claim 1 wherein the main valve comprises a first diaphragm valve with first and second actuating chambers disposed on opposite sides of the diaphragm, the area of the diaphragm exposed to the first chamber being smaller than the area of the diaphragm exposed to the second chamber, whereby the first diaphragm valve will remain closed when the pressures in the first and second chambers are substantially the same and will open when the pressure in the second chamber falls below the pressure in the first chamber by a pre-set amount.

11. A demand valve resuscitator for controlling the flow of breathable gas from a pressurized source to a patient comprising:

a) a housing having an inlet port adapted to be connected to the pressurized gas source, an outlet port adapted to be connected to the patient's airway, and an inhalation chamber disposed between the inlet and outlet ports;

b) a normally-closed-pressure-actuated main valve disposed in the housing between the inlet port and the inhalation chamber;

c) a main valve controller disposed in the housing and responsive to the pressure in the inhalation chamber for selectively opening and closing the main valve;

d) a normally-closed-manually operated bypass valve disposed in the housing for connecting the inlet to the inhalation chamber to supply gas from the pressurized source to the inhalation chamber independently of the main valve; and e) an outlet valve disposed between the inhalation chamber and the outlet for allowing gas from the pressurized source to pass from the inhalation chamber through the outlet port and enter the patient's airway and for venting to atmosphere back pressure at the outlet port.

12. The invention of claim 11 wherein the main valve comprises a first diaphragm valve with first and second actuating chambers disposed on opposite sides of the diaphragm, the area of the diaphragm exposed to the first chamber being smaller than the area of the diaphragm exposed to the second chamber, whereby the first diaphragm valve will remain closed when the pressures in the first and second chambers are substantially the same and will open when the pressure in the second chamber falls below the pressure in the first chamber by a pre-set amount.

13. The invention of claim 12 wherein both chambers of the first diaphragm valve are connected to the inlet port, the connection to the second chamber including a restrictor for restricting the flow rate.

14. The invention of claim 13 wherein the main valve controller includes a normally-closed second valve which opens the second chamber of the first diaphragm valve to atmosphere when the pressure within the inhalation chamber is below a predetermined value to allow the main valve to open and supply demand gas to the individual.

15. The invention of claim 14 wherein the second valve is a diaphragm valve with first and second chambers on opposite sides of the diaphragm, the first chamber of the second valve being vented to atmosphere and the second chamber thereof being in fluid communication with the inhalation chamber, whereby the second valve is in the open position when the pressure within the inhalation chamber is sub-atmospheric.

16. The invention of claim 11 further including a pressure relief valve in fluid communication with the inhalation chamber for setting the maximum allowable gas pressure within the inhalation chamber.

17. The invention of claim 16 wherein the pressure relief valve further includes a manual control for adjusting the pressure setting of the regulator.

18. The invention of claim 17 wherein the manual control for the pressure relief valve includes a manually-moveable cam which sets the maximum pressure in accordance with the position of the cam relative to the relief valve.

19. The invention of claim 18 wherein the relief valve is spring biased and the cam adjusts the force of the spring and thereby the pressure required to open the relief valve.

20. The invention of claim 19 wherein the cam is annular in shape with the opening force varying with the angular position of the cam, the manual control further including a rotatable knob connected to the cam for adjusting the angular position thereof.

21. The invention of claim 11 further including a manual control for presetting the maximum flow rate of gas through the bypass valve.

22. The invention of claim 11 wherein the housing includes an exhalation port and wherein the outlet valve connects the outlet port to the exhalation port when venting back pressure to atmosphere.

23. The invention of claim 22 further including a pressure relief valve in fluid communication with the inhalation chamber for setting the maximum allowable gas pressure within the inhalation chamber.

24. The invention of claim 23 further including an audible alarm disposed in fluid communication between the inhalation chamber and the pressure regulator.

25. A demand valve resuscitator for controlling the flow of breathable gas from a pressurized source to a patient comprising:

a) a housing having an inlet port adapted to be connected to the pressurized gas source and an outlet port adapted to be connected to the patient's airway;

b) a normally-closed-pressure-actuated main valve disposed in the housing;

c) a main valve controller disposed in the housing for opening the main valve when the pressure in the outlet port is below atmospheric pressure and for closing the main valve when the pressure in the outlet port rises to substantially atmospheric pressure;

d) a pressure relief valve in fluid communication with the outlet port when gas is flowing into the outlet port for setting the maximum allowable gas pressure within the outlet port, the pressure relief valve including a manual control for adjusting the pressure of the regulator;

e) a manually-operated bypass valve connecting the inlet to the outlet, the bypass valve including a manual control for presetting the maximum opening of the bypass valve;

f) an outlet valve disposed adjacent the outlet port for passing gas through the outlet port and for venting to atmosphere back pressure at the outlet port; and g) an audible alarm connected in series between the outlet port and the pressure regulator.

* * * * *